United States Patent
He et al.

(10) Patent No.: US 12,194,070 B2
(45) Date of Patent: Jan. 14, 2025

(54) TRADITIONAL CHINESE MEDICINE COMPOUND FOR IMPROVING TESTICULAR DYSFUNCTION, PREPARATION METHOD AND APPLICATION THEREOF

(71) Applicants: Ningxia Medical University, Yinchuan (CN); Ningxia Freedom Biological Pharmaceutical Technology Co., LTD, Yinchuan (CN)

(72) Inventors: Rui He, Yinchuan (CN); Guangyong Li, Yinchuan (CN); Xiaojiang Chen, Yinchuan (CN); Xiaoli Du, Yinchuan (CN); Xiangdong Zhu, Yinchuan (CN); Huiming Ma, Yinchuan (CN); Miao Sun, Yinchuan (CN); Jiafuruzi He, Yinchuan (CN)

(73) Assignees: Ningxia Medical University, Yinchuan (CN); Ningxia Freedom Biological Pharmaceutical Technology Co., LTD, Yinchuan (CN)

( * ) Notice: Subject to any disclaimer, the term of this patent is extended or adjusted under 35 U.S.C. 154(b) by 0 days.

(21) Appl. No.: 18/621,062

(22) Filed: Mar. 28, 2024

(65) Prior Publication Data
US 2024/0325478 A1    Oct. 3, 2024

(30) Foreign Application Priority Data
Mar. 29, 2023    (CN) .......................... 202310316037.4

(51) Int. Cl.
| | | |
|---|---|---|
| A61K 36/00 | (2006.01) |
| A61K 36/076 | (2006.01) |
| A61K 36/185 | (2006.01) |
| A61K 36/232 | (2006.01) |
| A61K 36/235 | (2006.01) |
| A61K 36/236 | (2006.01) |
| A61K 36/24 | (2006.01) |
| A61K 36/284 | (2006.01) |
| A61K 36/344 | (2006.01) |
| A61K 36/48 | (2006.01) |
| A61K 36/481 | (2006.01) |
| A61K 36/484 | (2006.01) |
| A61K 36/54 | (2006.01) |
| A61K 36/62 | (2006.01) |
| A61K 36/67 | (2006.01) |
| A61K 36/714 | (2006.01) |
| A61K 36/754 | (2006.01) |
| A61K 36/894 | (2006.01) |
| A61K 36/9062 | (2006.01) |
| A61K 36/9068 | (2006.01) |
| A61P 15/08 | (2006.01) |

(52) U.S. Cl.
CPC .......... *A61K 36/232* (2013.01); *A61K 36/076* (2013.01); *A61K 36/185* (2013.01); *A61K 36/235* (2013.01); *A61K 36/236* (2013.01); *A61K 36/24* (2013.01); *A61K 36/284* (2013.01); *A61K 36/344* (2013.01); *A61K 36/48* (2013.01); *A61K 36/481* (2013.01); *A61K 36/484* (2013.01); *A61K 36/54* (2013.01); *A61K 36/62* (2013.01); *A61K 36/67* (2013.01); *A61K 36/714* (2013.01); *A61K 36/754* (2013.01); *A61K 36/894* (2013.01); *A61K 36/9062* (2013.01); *A61K 36/9068* (2013.01); *A61P 15/08* (2018.01); *A61K 2236/331* (2013.01)

(58) Field of Classification Search
CPC .................................................... A61K 36/344
See application file for complete search history.

*Primary Examiner* — Qiuwen Mi

(57) ABSTRACT

A traditional Chinese medicine compound for improving testicular dysfunction is made from the following raw materials: *Codonopsis pilosula, Astragalus membranaceus, Dioscorea opposita, Angelica sinensis, Atractylodes macrocephala, Poria cocos, Cynanchum otophyllum, Psoralea corylifolia, Ligusticum chuanxiong, Nelumbo nucifera, Euryale ferox, Amomum villosum, Alpinia katsumadai, Foeniculum vulgare, Cinnamomum cassia, Evodia ruticarpa, Piper nigrum, Zingiber officinale, Aconitum carmichaelii,* and *Glycyrrhiza uralensis*. All the raw materials are combined, so that the spleen, the stomach and the kidney are in harmony, the qi, the blood and the body fluid are recovered, and the kidney essence is active. Animal experiments show that the traditional Chinese medicine compound can up-regulate expressions of phosphatidylinositol 3-kinase (PI3K), phospho-protein kinase B (p-AKT) and B-cell lymphoma-2 (Bcl-2), improve testicular dysfunction, improve hormone secretion, regulate a male reproductive endocrine environment of the body, and further improve semen parameters.

6 Claims, 7 Drawing Sheets

TRADITIONAL CHINESE MEDICINE COMPOUND FOR IMPROVING TESTICULAR DYSFUNCTION, PREPARATION METHOD AND APPLICATION THEREOF

TECHNICAL FIELD

The disclosure relates to the technical field of medicine, and particularly to a traditional Chinese medicine compound for improving testicular dysfunction, a preparation method and an application thereof.

BACKGROUND

Diabetes (i.e., diabetes mellitus) is one of the most important public health problems in modern times, and 90% of diabetic patients have type 2 diabetes mellitus (T2DM). Studies have shown that the diabetes can cause oligoasthenotspermia (Kong Z L, Sudirman S, Hsu Y C, et al., Fucoxanthin-Rich Brown Algae Extract Improves Male Reproductive Function on Streptozotocin-Nicotinamide-Induced Diabetic Rat Model, Int J Mol Sci, 2019, 20 (18)), in about half of male diabetic patients, an incidence of testicular dysfunction is as high as 95%, and more than 50% of the diabetic patients have infertility to varied degrees (Li Wenmei, Clinical study on serum reproductive hormones and semen quality in male diabetic patients, Diabetes New World, 2020, 23 (05): 23-25). Patients with oligoasthenotspermia account for about 75% of male infertility cases (Li Xinyang, Sun Zixue, Based on network pharmacology and molecular docking to explore the effect of Yishen Tongluo Buqi recipe on estrogen receptor in mice with oligoasthenotspermia, Chinese traditional patent medicine, 2021, 43 (11): 3216-3221.).

Because germ cells are extremely susceptible to medicines, so it is crucial to explore natural effective treatment methods with low side effects to improve and treat oligoasthenotspermia caused by disorder of glucose and lipid metabolism. At present, little attention has been paid to the oligoasthenotspermia caused by T2DM. Western medicine mainly treats the T2DM by surgery, reducing blood sugar and antioxidation, but this method will have significant side effects. Traditional Chinese medicine has advantages of personalization, good curative effect and few side effects, but it has not yet formed an effective scheme to improve testicular dysfunction in obese type 2 diabetes mellitus (i.e., diabesity, also referred to as T2DM in obese patients).

SUMMARY

The disclosure aims to make up for the shortcomings of the related art and provide a traditional Chinese medicine compound, which can improve hormone secretion, regulate a male reproductive endocrine environment of the body, improve semen parameters and improve testicular dysfunction.

In order to solve the above problem, the disclosure provides a traditional Chinese medicine compound for improving testicular dysfunction, which is made from the following raw materials: *Codonopsis pilosula, Astragalus membranaceus, Dioscorea* opposite (also referred to as Chinese yam), *Angelica sinensis, Atractylodes macrocephala, Poria cocos, Cynanchum otophyllum, Psoralea corylifolia, Ligusticum chuanxiong, Nelumbo nucifera, Euryale ferox, Amomum villosum, Alpinia katsumadai, Foeniculum vulgare, Cinnamomum cassia, Evodia ruticarpa, Piper nigrum, Zingiber officinale, Aconitum carmichaelii,* and *Glycyrrhiza uralensis.*

In an embodiment, the traditional Chinese medicine compound is made from the following raw materials in parts by weight: 10-40 parts of the *Codonopsis pilosula*, 15-100 parts of the *Astragalus membranaceus*, 10-40 parts of the *Dioscorea opposita*, 6-25 parts of the *Angelica sinensis*, 6-40 parts of the *Atractylodes macrocephala*, 10-30 parts of the *Poria cocos*, 10-30 parts of the *Cynanchum otophyllum*, 6-15 parts of the *Psoralea corylifolia*, 6-20 parts of the *Ligusticum chuanxiong*, 6-20 parts of the *Nelumbo nucifera*, 6-20 parts of the *Euryale ferox*, 3-10 parts of the *Amomum villosum*, 3-10 parts of the *Alpinia katsumadai*, 6-20 parts of the *Foeniculum vulgare*, 3-15 parts of the *Cinnamomum cassia*, 6-10 parts of the *Evodia ruticarpa*, 6-15 parts of the *Piper nigrum*, 6-15 parts of the *Zingiber officinale*, 6-15 parts of the *Aconitum carmichaelii*, and 6-10 parts of the *Glycyrrhiza uralensis*.

The disclosure further provides a method for preparing a traditional Chinese medicine compound for improving testicular dysfunction, including: mixing the raw materials described in the above technical scheme to obtain a mixture and extracting the mixture of the raw materials.

In an embodiment, a method for the extracting the mixture of the raw materials comprises: water extraction (i.e., decocting method).

In an embodiment, the water extraction includes: mixing the mixture of the raw materials with water according to a weight-volume ratio of 136-500 grams (g):400-1000 milliliters (mL), soaking the mixture of the raw materials in the water for 30 minutes (min), decocting the mixture of the raw materials soaked in the water on a high heat until the mixture of the raw materials soaked in the water boils to obtain boiled materials, decocting the boiled materials on a gentle heat for 40-60 min to obtain decocted materials, and filtering the decocted materials. In an embodiment, a temperature of the high heat is in a range of 200-300° C., and a temperature of the gentle heat is in a range of 100-200° C.

The disclosure further provides an application method of the traditional Chinese medicine compound described in the above technical scheme, including: applying the traditional Chinese medicine compound to prepare a product for improving the testicular dysfunction.

In an embodiment, the product includes: medicine or food; and the testicular dysfunction includes: a testicular dysfunction caused by diabetes mellitus.

In an embodiment, the testicular dysfunction caused by the diabetes includes: a testicular dysfunction caused by obese type 2 diabetes mellitus.

The disclosure further provides an application method of the traditional Chinese medicine compound described in the above technical scheme, including: applying the traditional Chinese medicine compound to prepare a product for improving testicular morphology and/or improving semen parameters.

The disclosure further provides a medicine for improving testicular dysfunction, including: the traditional Chinese medicine compound described in the above technical scheme and a pharmaceutically acceptable excipient.

Beneficial effects are as follows:

The disclosure uses *Codonopsis pilosula, Astragalus membranaceus, Dioscorea opposita, Angelica sinensis, Atractylodes macrocephala, Poria cocos, Cynanchum otophyllum, Psoralea corylifolia, Ligusticum chuanxiong, Nelumbo nucifera, Euryale ferox, Amomum villosum, Alpinia katsumadai, Foeniculum vulgare, Cinnamomum cassia, Evodia ruticarpa, Piper nigrum, Zingiber officinale,*

*Aconitum carmichaelii*, and *Glycyrrhiza uralensis* as the raw materials to prepare the traditional Chinese medicine compound. The *Codonopsis pilosula*, the *Astragalus membranaceus*, the *Dioscorea opposita* and the *Cynanchum otophyllum* act as monarch drugs (also referred to as principal drugs or sovereign drugs) to tonify qi, nourish yin, generate body fluids, nourish blood, and tonify the spleen to nourish the kidneys. The *Atractylodes macrocephala*, the *Poria cocos*, the *Euryale ferox* and the *Psoralea corylifolia* act as minister drugs to reduce dampness and turbidity in the spleen and stomach, and warm and nourish the kidney yang. The *Angelica sinensis*, the *Ligusticum chuanxiong*, the *Nelumbo nucifera*, the *Amomum villosum*, the *Foeniculum vulgare*, the *Cinnamomum cassia*, the *Piper nigrum*, the *Zingiber officinale*, the *Alpinia katsumadai*, the *Evodia ruticarpa* and the *Aconitum carmichaelii* act as adjuvant drugs, the *Angelica sinensis* and the *Ligusticum chuanxiong* can enrich the blood, promote blood circulation, improve microcirculation, and restore spermatogenic function. The *Nelumbo nucifera* can clear heart-fire. The *Cinnamomum cassia* and the *Aconitum carmichaelii* can warm yang and invigorating qi, stimulate the circulation of qi and blood, guide fire back to its origin, and the kidney yang can be warmed to achieve water evaporation to nourish the yin of five internal organs (i.e., heart, liver, spleen, lungs and kidneys). The *Piper nigrum*, the *Amomum villosum*, the *Foeniculum vulgare*, and the *Zingiber officinale* can promote the circulation of qi and warm the middle burner, strengthen the spleen and qi and facilitate the proper transformation and transportation of essential nutrients. The *Glycyrrhiza uralensis* acts as an envoy drug to balance and harmonize the actions of other medicine in the formula. The disclosure reasonably selects the raw materials, and all the drugs are combined, so that the spleen, the stomach and the kidney are in harmony, the qi, the blood and the body fluid are recovered, and the kidney essence is active. Animal experiments show that the traditional Chinese medicine compound provided by the disclosure can up-regulate expressions of phosphatidylinositol 3-kinase (PI3K), phospho-protein kinase B (p-AKT) and B-cell lymphoma-2 (Bcl-2), improve testicular dysfunction, improve hormone secretion, regulate a male reproductive endocrine environment of the body, and further improve semen parameters.

BRIEF DESCRIPTION OF DRAWINGS

In order to more clearly explain the technical schemes in embodiments of the disclosure or in the related art, the drawings needed in the embodiments will be briefly introduced below.

DETAILED DESCRIPTION OF EMBODIMENTS

Figure 1A:
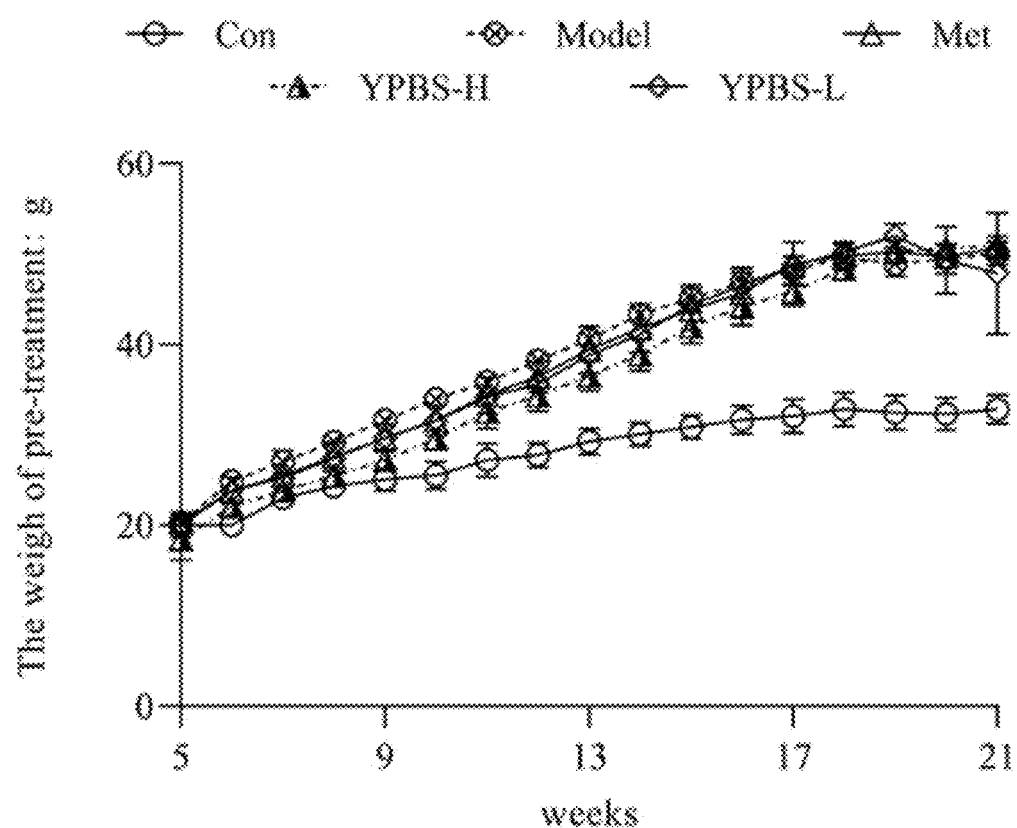
FIGS. 1A and 1B illustrate schematic diagrams showing effects of different treatments on weights of mice with testicular dysfunction caused by obese type 2 diabetes mellitus.

The disclosure provides a traditional Chinese medicine compound for improving testicular dysfunction, made from the following raw materials:

*Codonopsis pilosula, Astragalus membranaceus, Dioscorea opposita, Angelica sinensis, Atractylodes macrocephala, Poria cocos, Cynanchum otophyllum, Psoralea corylifolia, Ligusticum chuanxiong, Nelumbo nucifera, Euryale ferox, Amomum villosum, Alpinia katsumadai, Foeniculum vulgare, Cinnamomum cassia, Evodia ruticarpa, Piper nigrum, Zingiber officinale, Aconitum carmichaelii,* and *Glycyrrhiza uralensis*.

The raw materials include the *Codonopsis pilosula*, the parts by weight of the *Codonopsis pilosula* is preferably 10-40 parts, further preferably 15-35 parts, more preferably 20-30 parts, and most preferably 25 parts.

The raw materials include the *Astragalus membranaceus*, based on the parts by weight of the *Codonopsis pilosula*, the parts by weight of the *Astragalus membranaceus* is preferably 15-100 parts, further preferably 20-80 parts, more preferably 30-60 parts, and most preferably 40-50 parts.

The raw materials include the *Dioscorea opposita*, based on the parts by weight of the *Codonopsis pilosula*, the parts by weight of the *Dioscorea opposita* is preferably 10-40 parts, further preferably 15-35 parts, more preferably 20-30 parts, and most preferably 25 parts.

The raw materials include the *Cynanchum otophyllum*, based on the parts by weight of the *Codonopsis pilosula*, the parts by weight of the *Cynanchum otophyllum* is preferably 10-30 parts, further preferably 15-25 parts, and more preferably 20 parts.

The disclosure takes the *Codonopsis pilosula*, the *Astragalus membranaceus*, the *Dioscorea opposita* and the *Cynanchum otophyllum* as monarch drugs to tonify qi, nourish yin, generate body fluids, nourish blood, and tonify the spleen to nourish the kidneys.

The raw materials include the *Atractylodes macrocephala*, based on the parts by weight of the *Codonopsis pilosula*, the parts by weight of the *Atractylodes macrocephala* is preferably in 6-40 parts, further preferably 10-35 parts, more preferably 20-30 parts, and most preferably 25 parts.

The raw materials include the *Poria cocos*, based on the parts by weight of the *Codonopsis pilosula*, the parts by weight of the *Poria cocos* is preferably 10-30 parts, further preferably 15-25 parts, and more preferably 20 parts.

The raw materials include the *Euryale ferox*, based on the parts by weight of the *Codonopsis pilosula*, the parts by weight of the *Euryale ferox* is preferably 6-20 parts, further preferably 8-15 parts, and more preferably 10 parts.

The raw materials include the *Psoralea corylifolia*, based on the parts by weight of the *Codonopsis pilosula*, the parts by weight of the *Psoralea corylifolia* is preferably 6-15 parts, and further preferably 8-10 parts.

The disclosure takes the *Atractylodes macrocephala*, the *Poria cocos*, the *Euryale ferox*, and the *Psoralea corylifolia* as minister drugs to reduce dampness and turbidity in the spleen and stomach, and warm and nourish the kidney yang.

The raw materials include the *Angelica sinensis*, based on the parts by weight of the *Codonopsis pilosula*, the parts by weight of the *Angelica sinensis* is preferably 6-25 parts, further preferably 8-20 parts, and more preferably 10-15 parts.

The raw materials include the *Ligusticum chuanxiong*, based on the parts by weight of the *Codonopsis pilosula*, the parts by weight of the *Ligusticum chuanxiong* is preferably 6-20 parts, further preferably 8-15 parts, and more preferably 10 parts.

The raw materials include the *Nelumbo nucifera*, based on the parts by weight of the *Codonopsis pilosula*, the parts by weight of the *Nelumbo nucifera* is preferably 6-20 parts, further preferably 8-15 parts, and more preferably 10 parts.

The raw materials include the *Amomum villosum*, based on the parts by weight of the *Codonopsis pilosula*, the parts by weight of the *Amomum villosum* is preferably 3-10 parts, and further preferably 5-8 parts.

The raw materials include the *Foeniculum vulgare*, based on the parts by weight of the *Codonopsis pilosula*, the parts by weight of the *Foeniculum vulgare* is preferably 6-20 parts, further preferably 8-15 parts, and more preferably 10 parts. The *Foeniculum vulgare* used in the disclosure may be the *Foeniculum vulgare* mill (i.e., Fennel).

The raw materials include the *Cinnamomum cassia*, based on the parts by weight of the *Codonopsis pilosula*, the parts by weight of the *Cinnamomum cassia* is preferably 3-15 parts and further preferably 8-10 parts.

The raw materials include the *Piper nigrum*, based on the parts by weight of the *Codonopsis pilosula*, the parts by weight of the *Piper nigrum* is preferably 6-15 parts and further preferably 8-10 parts. The *Piper nigrum* used in the disclosure may be white pepper.

The raw materials include the *Zingiber officinale*, based on the parts by weight of the *Codonopsis pilosula*, the parts by weight of the *Zingiber officinale* is preferably 6-15 parts and further preferably 8-10 parts.

The raw materials include the *Alpinia katsumadai*, based on the parts by weight of the *Codonopsis pilosula*, the parts by weight of the *Alpinia katsumadai* is preferably 3-10 parts and further preferably 5-9 parts.

The raw materials include the *Evodia ruticarpa*, based on the parts by weight of the *Codonopsis pilosula*, the parts by weight of the *Evodia ruticarpa* is preferably 6-10 parts and further preferably 8-10 parts.

The raw materials include the *Aconitum carmichaelii*, based on the parts by weight of the *Codonopsis pilosula*, the parts by weight of the *Aconitum carmichaelii* is preferably 6-15 parts and further preferably 8-15 parts.

The disclosure takes the *Angelica sinensis*, the *Ligusticum chuanxiong*, the *Nelumbo nucifera*, the *Amomum villosum*, the *Foeniculum vulgare*, the *Cinnamomum cassia*, the *Piper nigrum*, the *Zingiber officinale*, the *Alpinia katsumadai*, the *Evodia ruticarpa* and the *Aconitum carmichaelii* as adjuvant drugs, the *Angelica sinensis* and the *Ligusticum chuanxiong* can enrich the blood, promote blood circulation, improve microcirculation, and restore spermatogenic function; the *Nelumbo nucifera* can clear heart-fire; the *Cinnamomum cassia* and the *Aconitum carmichaelii* can warm yang and invigorating qi, stimulate the circulation of qi and blood, guide fire back to its origin, and the kidney yang can be warmed to achieve water evaporation to nourish the yin of the five internal organs; the *Piper nigrum*, the *Amomum villosum*, the *Foeniculum vulgare*, and the *Zingiber officinale* can promote the circulation of qi and warm the middle burner, strengthen the spleen and qi and facilitate the proper transformation and transportation of essential nutrients.

The raw materials include the *Glycyrrhiza uralensis*, based on the parts by weight of the *Codonopsis pilosula*, the parts by weight of the *Glycyrrhiza uralensis* is preferably 6-10 parts and further preferably 8 parts.

The disclosure takes the *Glycyrrhiza uralensis* as an envoy drug to balance and harmonize actions of other medicine in the formula.

The disclosure reasonably selects the raw materials, and all the drugs are combined, so that the spleen, the stomach and the kidney are in harmony, the qi, the blood and the body fluid are recovered, and the kidney essence is active.

The disclosure further provides a method for preparing a traditional Chinese medicine compound for improving testicular dysfunction, including: mixing the raw materials described in the technical scheme to obtain a mixture and extracting the mixture of the raw materials.

The disclosure mixes the raw materials described in the technical scheme and extracts them. In the disclosure, a method for extracting the mixture of the raw materials is water extraction.

In the disclosure, a method for the water extraction preferably includes: mixing the mixture of the raw materials with water according to a weight-volume ratio of 136-500 g:400-1000 mL, soaking the mixture of the raw materials in the water for 30 min, decocting the mixture of the raw materials soaked into the water on a high heat until boiling to obtain boiled materials, decocting the boiled materials on a gentle heat for 40-60 min to obtain decocted materials, followed by filtering the decocted materials to obtain an extract, which is the traditional Chinese medicine compound. The weight-volume ratio of the mixture to the water is preferably 140-450 g: 50-900 mL, more preferably 200-400 g: 500-800 mL, more preferably 250-350 g: 600-700 mL, and most preferably 300 g: 650 mL.

The disclosure preferably further provides an application of the traditional Chinese medicine compound described in the technical scheme in preparing an product for improving testicular dysfunction.

In the disclosure, the product preferably includes medicine or food. The testicular dysfunction preferably includes a testicular dysfunction caused by diabetes, and further preferably includes a testicular dysfunction caused by T2DM.

Mice experiments show that the traditional Chinese medicine compound provided by the disclosure can up-regulate expressions of PI3K, p-AKT and Bcl-2 in mice, significantly increase levels of total superoxide dismutase (T-SOD) and glutathione peroxidase (GHX-px), and down-regulate a level of malondialdehyde (MDA), effectively improving a level of oxidative stress in male animals and inhibiting an interference of reproductive cell apoptosis and oxidative stress on spermatogenesis caused by the increase of the level of reactive oxygen species (ROS), thereby increasing the testosterone level of mice with obese type 2 diabetes mellitus and improving semen parameters. The traditional Chinese medicine compound provided by the disclosure can also significantly increase glucose intake, the sensitivity of islet is enhanced, and the effect is similar to that of metformin, and it can also improve T2DM to some extent.

The disclosure further provides an application of the traditional Chinese medicine compound described in the technical scheme in preparing a product for improving testicular morphology and/or improving semen parameters.

The disclosure further provides a medicine for improving testicular dysfunction, which includes the traditional Chinese medicine compound described in the technical scheme and a pharmaceutically acceptable excipient.

In the disclosure, a form of the medicine preferably includes any one of aqueous, granule and freeze-drying agents. The disclosure has no strict requirements on the type of the pharmaceutically acceptable excipient, and can be selected according to the form of the medicine.

In order to further illustrate the disclosure, a traditional Chinese medicine compound for improving testicular dysfunction provided by the disclosure, its preparation method and application will be described in detail with the attached drawings and embodiments, but they should not be understood as limiting the scope of protection of the disclosure.

Embodiment 1

A method for preparing a traditional Chinese medicine compound for improving testicular dysfunction includes the following steps.

(1) Preparing Raw Materials:

20 g of *Codonopsis pilosula,* 30 g of *Astragalus membranaceus,* 20 g of *Dioscorea opposita,* 20 g of *Angelica sinensis,* 10 g of *Atractylodes macrocephala,* 10 g of *Poria cocos,* 10 g of *Cynanchum otophyllum,* 10 g of *Ligusticum chuanxiong,* 10 g of *Nelumbo micifera,* 10 g of *Euryale ferox,* 10 g of *Psoralea corylifolia,* 5 g of *Amomum villosum,* 10 g of *Alpinia katsumadai,* 20 g of *Foeniculum vulgare,* 10 g of *Cinnamomum cassia,* 10 g of *Evodia ruticarpa,* 10 g of *Piper nigrum,* 10 g of *Zingiber officinale,* 10 g of *Aconitum carmichaelii,* and 10 g of *Glycyrrhiza uralensis.*

(2) All the raw materials in step (1) are put into a ceramic pot, 400 mL of water are added into the ceramic pot, the raw materials are soaked into the water for 30 minutes, the soaked materials in the ceramic pot are decocted on a high heat until them boils, then the materials in the ceramic pot are decocted on a gentle heat for 40-60 min, followed by filtering to obtain about 200 mL of the traditional Chinese medicine compound.

Application Example 1

1. Materials
1.1 Experimental Animals

Thirty male specific pathogen-free (SPF) C57BL/6J mice 4-weeks-old (18-22 g) are acquired from the Laboratory Animal Center of Ningxia Medical University (Approval No. 10752309202100163).

1.2 Experimental Conditions

The experimental site is a SPF laboratory of Laboratory Animal Center of Ningxia Medical University. The temperature is 22-23° C., the humidity is 50%-60%, day and night are alternated for 12 hours, the mice are free to eat and drink water, and the environment is quiet. The laboratory environment meets the conditions for raising clean animals.

1.3 Medicine

The medicine includes the traditional Chinese medicine compound obtained in the embodiment 1, high-fat feed bought from Research Diets (#D12492) in the US and metformin hydrochloride tablets (Sino-US Shanghai Squib, 0.5 g).

1.4 Main Reagents

The main reagent include: PI3K, protein kinase B (AKT), p-AKT, and Bcl-2 antibodies purchased from Cell Signaling Technology, and kits for measuring testosterone, T-SOD, MDA and GSH-px provided from Elabscience.

2. Method 2.1 Grouping and Modeling of Animals

With six mice in each group, the mice are randomly assigned after one week of adaptive rearing to a control group (Con), a model group (Model), a high-dose compound group (YPBS-H), a low-dose compound group (YPBS-L) and a metformin group (Metformin, Met). The six mice in the control group are given regular feed, the remaining mice are fed with 60% high-fat feed, the weight of each of mice is recorded every 7 days during the feeding. The results are shown in FIG. 1A.

According to FIG. 1A, it can be seen that the weight of the mice in the model group, the high-dose compound group, the low-dose compound group and the metformin group is increased obviously, and they are obviously obese. During the experiment, it is found that the random blood glucose of the mice in the model group is higher than 11.1 millimoles per liter (mmol/L), the blood glucose detected by oral glucose tolerance test (OGTT) and insulin tolerance test (ITT) is significantly higher than that of the control group, the sperm count, the sperm motility and the sperm viability are significantly lower than that of the control group, and the sperm malformation rate is significantly higher than that of the control group, which indicates that mouse models with obese type 2 diabetic mellitus are successfully established.

2.2 Administration

The mice in each group have been successfully established after feeding for 16 weeks in step 2.1, and the mice in each group are given medicine treatment as follows.

The control group (Con): normal saline is given.

The model group (T2DM): normal saline is given.

The high-dose compound group (YPBS-H): the traditional Chinese medicine compound obtained in the embodiment 1 is given at a dose of 4 grams per kilogram per day (g/kg/d) per animal.

The low-dose compound group (YPBS-L): the traditional Chinese medicine compound obtained in the embodiment 1 is given at a dose of 2 g/kg/d per animal.

The metformin group (Met): the metformin is given at a dose of 200 mg/kg/d per animal.

During the administration, the mice are fed with the normal feed and drink water normally, and the weight changes of mice are observed. Data is analyzed using GraphPad Prism 8.4 statistical software. Counting data of experimental results is expressed as rate/percentage (%), and measurement data is expressed as $\bar{x}$ (i.e., mean)±s. The one-way analysis of variance (ANOVA) is used to compare the groups, and the difference is statistically significant with $P<0.05$. The results are shown in Table 1 and FIG. 1B.

TABLE 1 comparison ($\bar{x} \pm s$) of the area under curve (AUC) of the weight of mice in each group and the weight on the 30$^{th}$ day after treatment of the mice in each group

| Group | AUC of weight before treatment | AUC of weight after treatment | Weight on the 30$^{th}$ day after treatment (g) |
|---|---|---|---|
| Con | 450.9 ± 4.3 | 1027.0 ± 13.4 | 31.3 ± 1.5 |
| Model | 654.5 ± 3.9* | 1629.0 ± 9.2* | 57.4 ± 2.5* |
| Met | 613.8 ± 5.3$^\Delta$ | 1243.0 ± 12.0$^{\Delta\Delta}$ | 37.9 ± 2.2$^\Delta$ |
| YPBS-H | 597.3 ± 5.4$^\Delta$ | 1335.0 ± 11.5$^{\Delta\blacktriangle}$ | 41.5 ± 1.4$^\Delta$ |
| YPBS-L | 612.7 ± 5.1$^\Delta$ | 1343.0 ± 21.9$^{\Delta\blacktriangle}$ | 42.4 ± 1.5$^{\Delta\blacktriangle}$ |

Note:.
*p < 0.01 as compared to the control group;
$^\Delta$p < 0.01 as compared to the model group;
$^\blacktriangle$p < 0.05 as compared to the metformin group; similarly hereinafter.

Figure 1B:
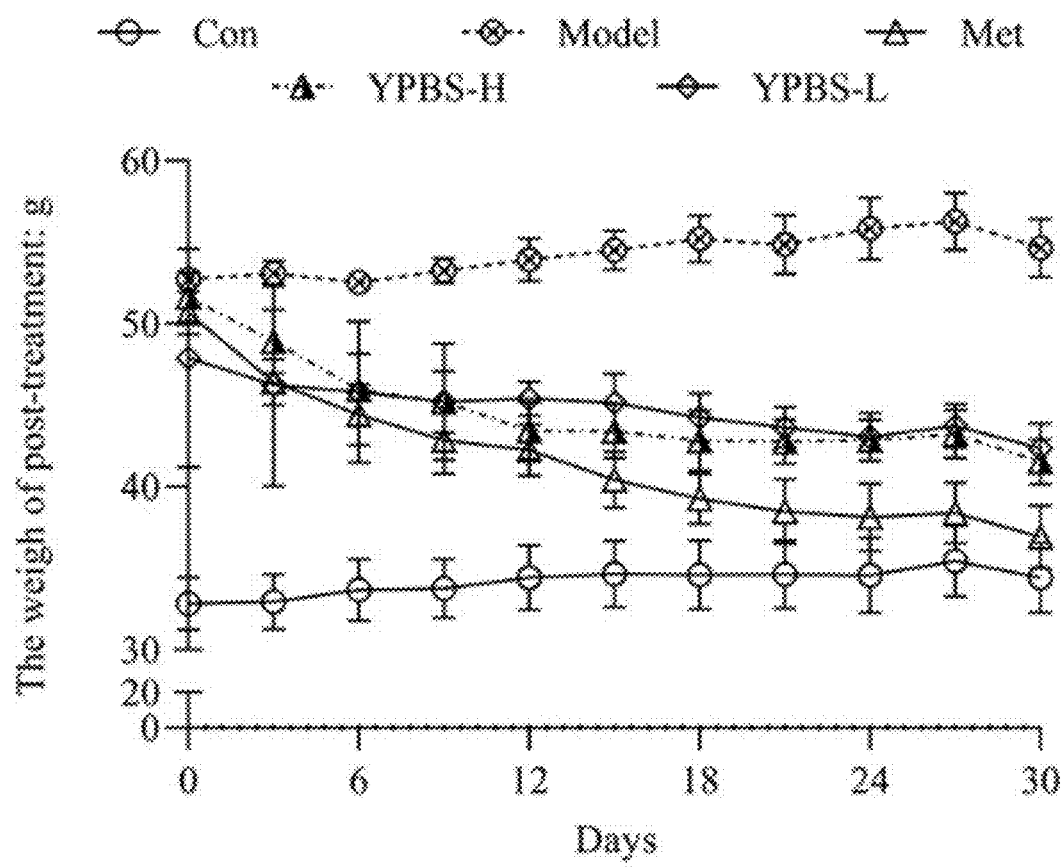

As can be seen from Table 1 and FIG. 1B, at 16 weeks, compared to the control group, the weight and AUC of the mice in the model group, the metformin group, the YPBS-H and YPBS-L groups show substantial increase (p<0.05), but there is no significant difference between the model group, metformin group, YPBS-H and YPBS-L groups (P>0.05). Compared to the model group, the weight and AUC of the mice in the metformin group, YPBS-H and YPBS-L groups show substantial decrease, and the weight and AUC of the mice in the metformin group are lower than that of the mice in the YPBS-H and YPBS-L groups (p<0.05). At treating 30 days, the weight of mice in the model group is substantially greater than that of mice in the control group, and the weight of the mice in the metformin group, YPBS-H and YPBS-L groups decreases significantly compared to the model group, and the weight of the mice in the metformin group is lower than that of the mice in the YPBS-L group (p<0.05), but there is no statistical significance compared with the YPBS-H group (P>0.05). The traditional Chinese medicine compound provided by the disclosure can improve the weight of obese type 2 diabetic mice with testicular dysfunction (i.e., the mice with testicular dysfunction caused by obese type 2 diabetic mellitus).

2.3 After 30 days of administration of each group in step 2.2, the following tests are performed in each group.

2.3.1 OGTT and ITT Tests

OGTT test: the mice are weighed after 15 h fast, fasting blood glucose (FPG) of the mice is measured separately, and the amount of glucose is determined based on the mice's weight. Blood glucose fluctuations are then monitored at 15 min, 30 min, 60 min and 120 min after gavage. Data is analyzed using GraphPad Prism 8.4 statistical software. Counting data of experimental results is expressed as rate/percentage (%), and measurement data is expressed as $\bar{x}\pm s$. The one-way ANOVA is used to compare the groups, and the difference is statistically significant with P<0.05. The results are shown in Table 2 and FIG. 2A.

ITT test: the mice are weighed after 5 h fast, the insulin dosage is calculated, and FPG of the mice is measured. Blood glucose fluctuations are then monitored at 15 min, 30 min, 60 min and 120 min after insulin is given. Data is analyzed using GraphPad Prism 8.4 statistical software. Counting data of experimental results is expressed as rate/percentage (%), and measurement data is expressed as $\bar{x}\pm s$. The one-way ANOVA is used to compare the groups, and the difference is statistically significant with P<0.05. The results are shown in Table 2 and FIG. 2B.

TABLE 2 comparation between OGTT-AUC, ITT-AUC and FPG of the mice in the respective groups

| Group | OGTT-AUC | ITT-AUC | FPG on the 30$^{th}$ day after treatment |
|---|---|---|---|
| Con | 1828.0 ± 103.3 | 607.7 ± 42.2 | 5.5 ± 0.63 |
| Model | 2416.0 ± 147.8* | 1172.0 ± 103.6* | 8.0 ± 0.6* |
| Met | 1660 ± 70.3$^\Delta$ | 760.7 ± 49.5$^\Delta$ | 5.5 ± 0.9$^\Delta$ |
| YPBS-H | 1847.0 ± 75.8$^\Delta$ | 689.8 ± 55.9$^{\Delta\blacktriangle}$ | 5.4 ± 1.0$^\Delta$ |
| YPBS-L | 2156.0 ± 303.2$^\Delta$ | 787.9 ± 52.7$^\Delta$ | 6.6 ± 1.0 |

Figure 2A:
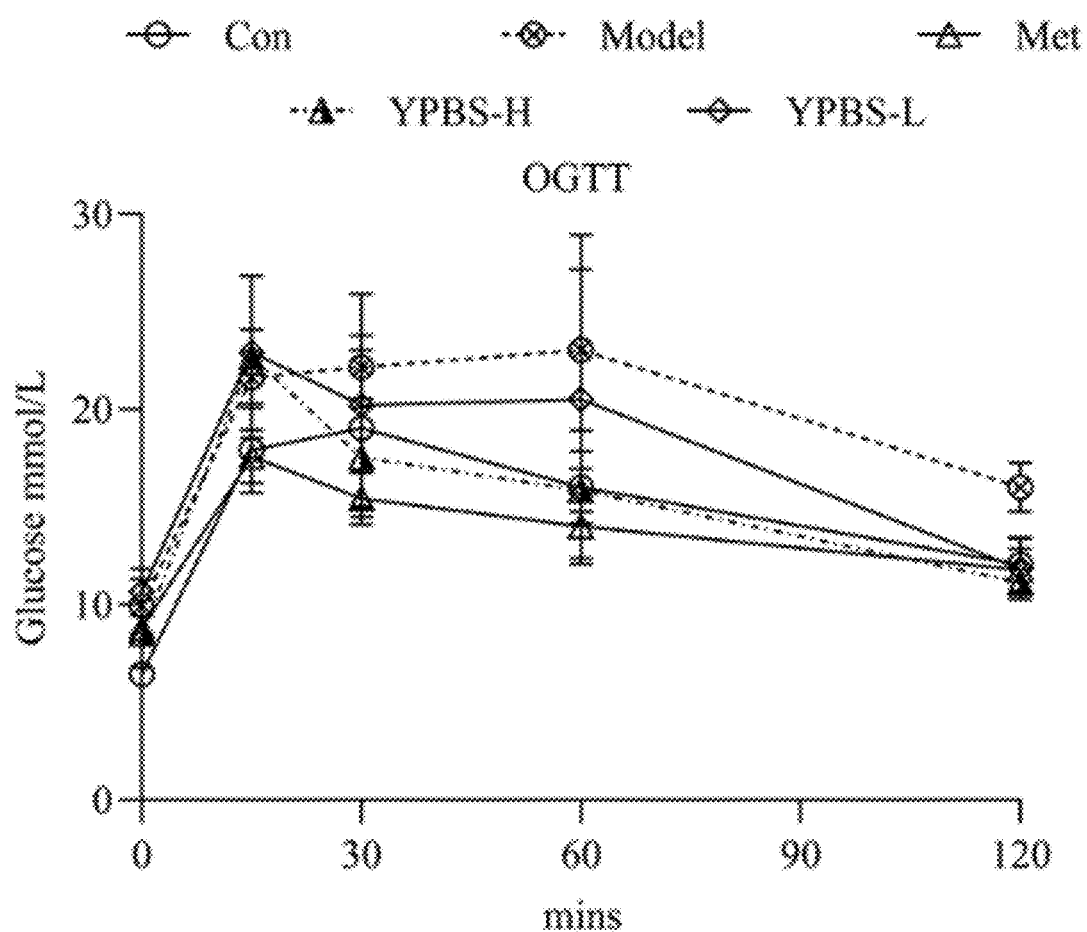
FIGS. 2A and 2B illustrate schematic diagrams showing effects of different treatments on blood glucose of mice with testicular dysfunction caused by obese type 2 diabetes mellitus.
Figure 2B:
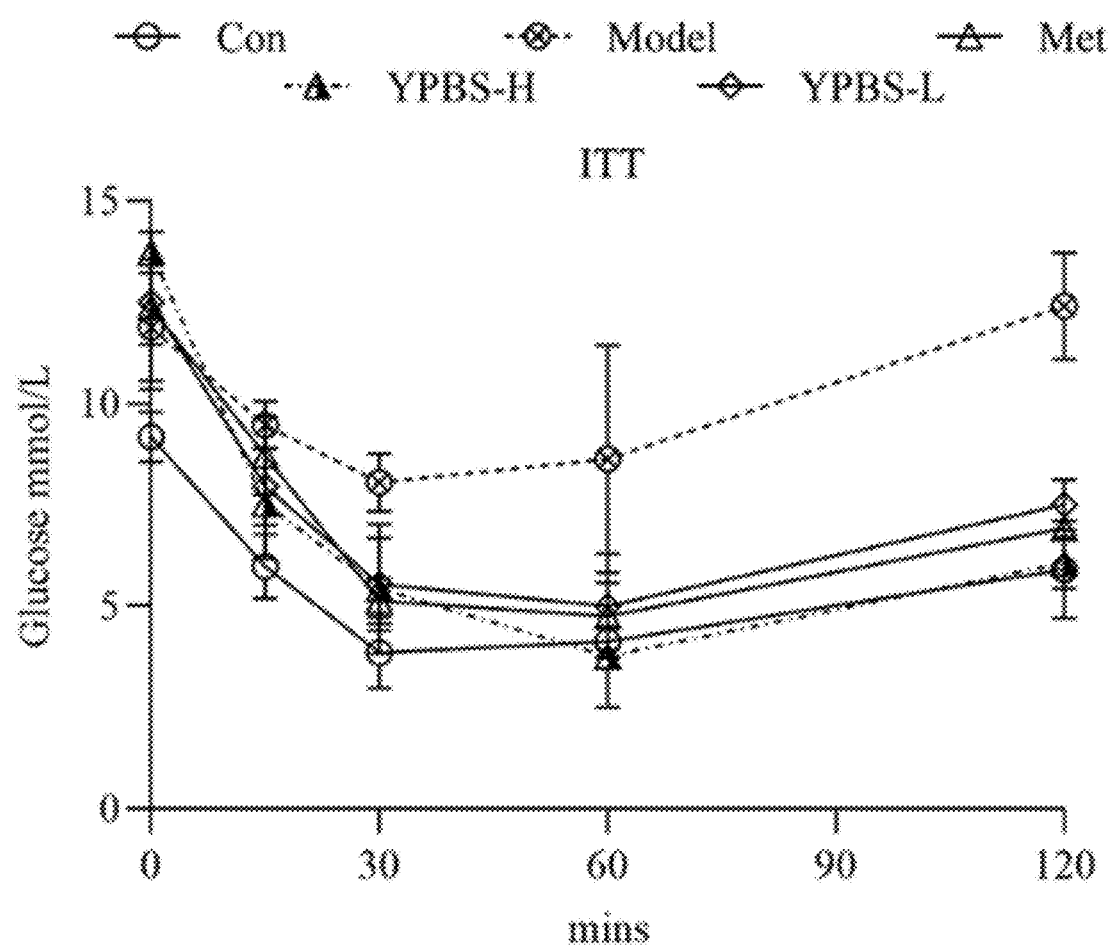
Figure 3A:
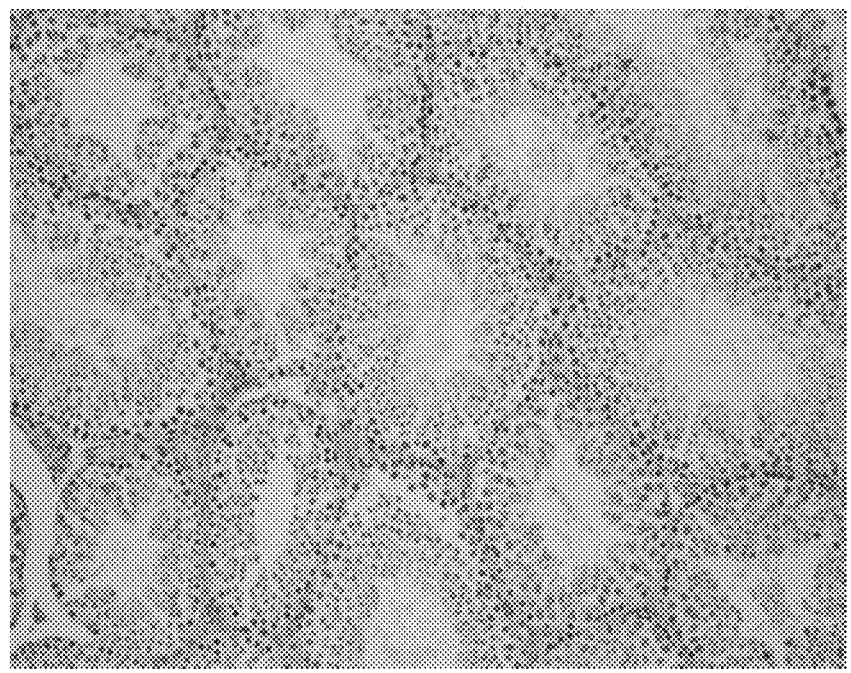
FIG. 3A illustrates a hematoxylin and eosin (HE) staining diagram showing an effect on testicular morphology of mice with testicular dysfunction caused by obese type 2 diabetes mellitus in a control group (200×).
Figure 3B:
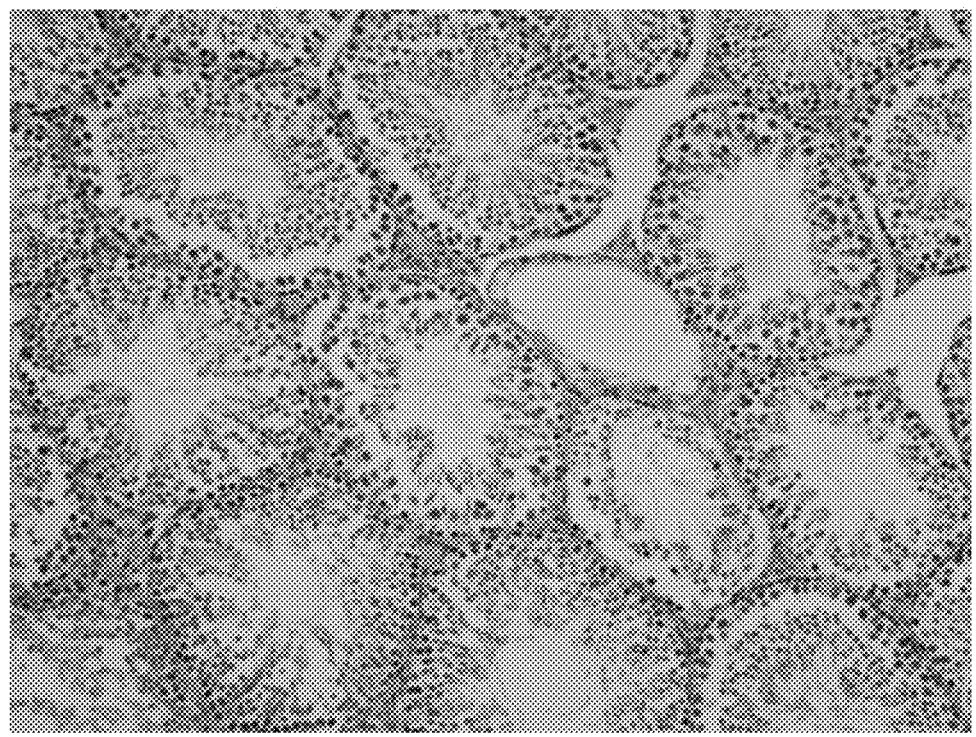
FIG. 3B illustrates a HE staining diagram showing an effect on testicular morphology of mice with testicular dysfunction caused by obese type 2 diabetes mellitus in a model group (200×).
Figure 3C:
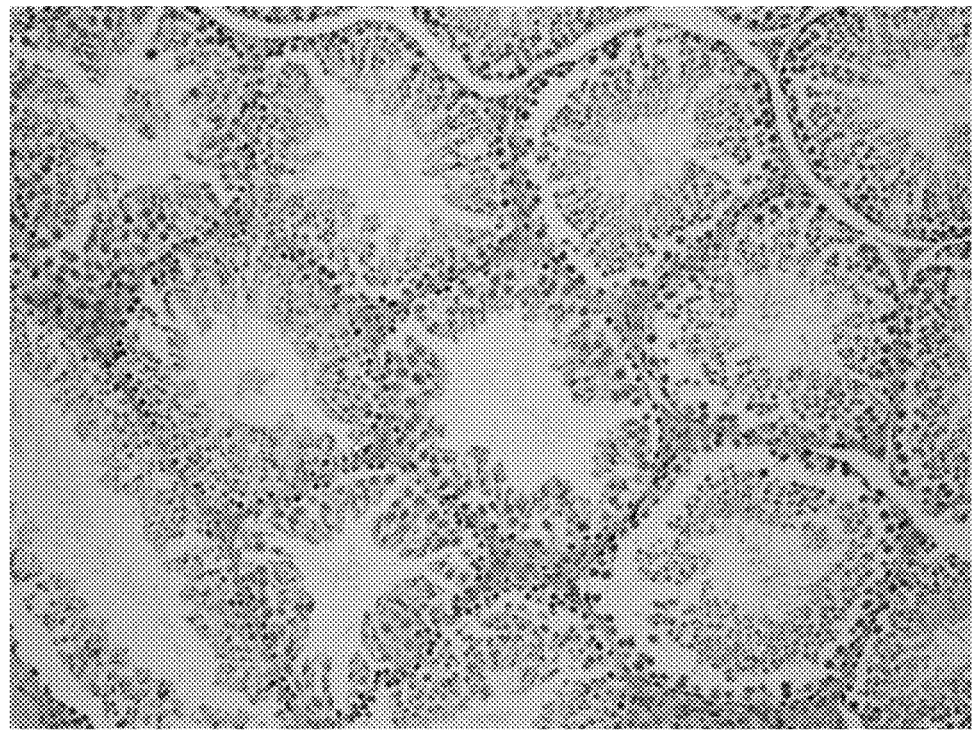
FIG. 3C illustrates a HE staining diagram showing an effect on testicular morphology of mice with testicular dysfunction caused by obese type 2 diabetes mellitus in a metformin group (200×).
Figure 3D:
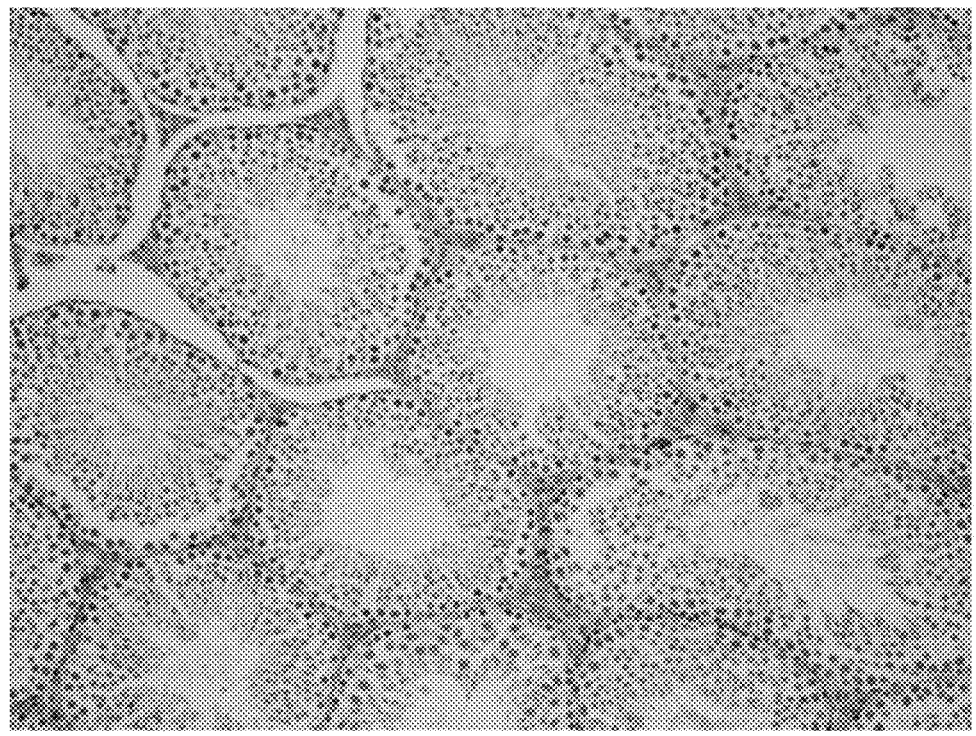
FIG. 3D illustrates a HE staining diagram showing an effect on testicular morphology of mice with testicular dysfunction caused by obese type 2 diabetes mellitus in a high-dose compound group (200×).
Figure 3E:
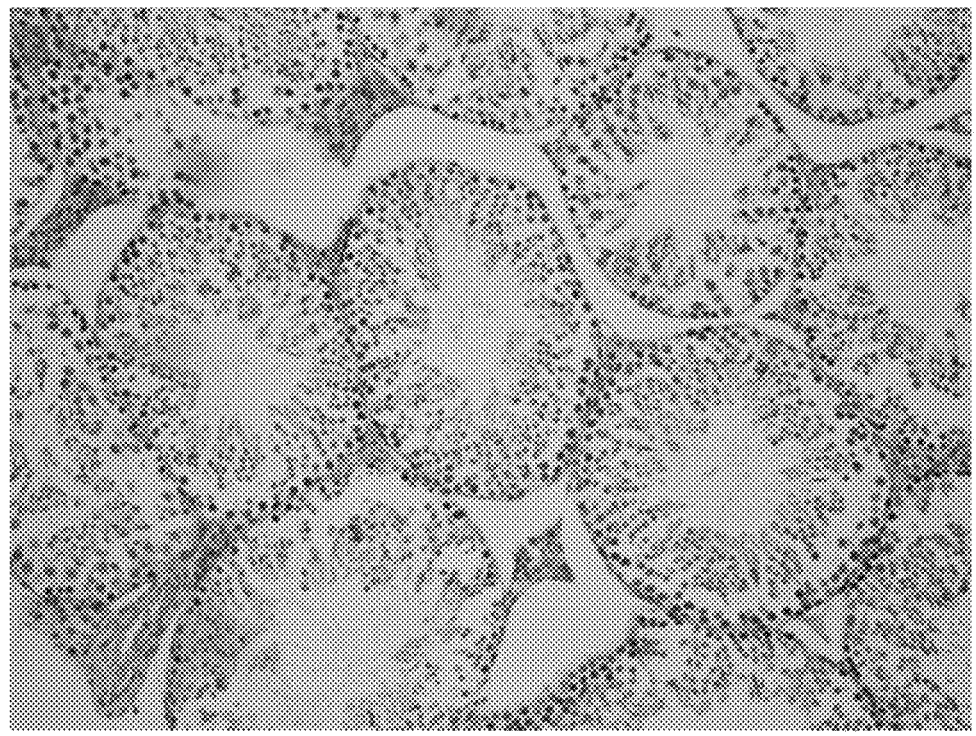
FIG. 3E illustrates a HE staining diagram showing an effect on testicular morphology of mice with testicular dysfunction caused by obese type 2 diabetes mellitus in a low-dose compound group (200×).

According to Table 2 and FIGS. 2A-2B, the FPG and the blood glucose at 15, 30, 60 and 120 min after gavage are measured in the OGTT, and the blood glucose level of the model group is significantly higher than that of the control group, the glucose uptake of the YPBS-H group and the metformin group is significantly improved, and the OGTT-AUC of the mice in the model group is significantly increased (p<0.05), indicating the formation of diabetes state. OGTT-AUC is decreased significantly in the metformin and YPBS-H groups compared to the model group (p<0.05), indicating the boost of glucose absorption. The FPG and blood glucose at 15, 30, 60 and 120 min after giving the insulin are measured in the ITT, the similar results are obtained, however, the YPBS-H group is superior to the metformin group (p<0.05). The traditional Chinese medicine compound of the disclosure might improve islet function sensitivity and boost glucose absorption. Furthermore, compared to the model group, the YPBS-H group and metformin group significantly lower fasting blood glucose in the mice (p<0.05).

2.3.2 Detection of Testicular Morphology

HE staining is performed on mouse testis tissue, and the results are shown in FIG. 3A to FIG. 3E.

As shown in FIG. 3A to FIG. 3E, the testicular tissue structure of the mice in the control group (FIG. 3A) is clear, the spermatogenic cells at all levels in the seminifertogenic tubules are neatly arranged, spermatogonia, primary spermatoblasts, secondary spermatoblasts, sperm cells, etc. can be seen on the basal surface, and mature sperm can be seen in the cavity. The testicular tissue structure of the mice in the model group (FIG. 3B) is chaotic, as is the organization of the spermatogenic cells at all levels, which is greatly decreased, and a widely area of voids emerges in the cavity. The testicular morphology of the mice in the metformin group (FIG. 3C), YPBS-H group (FIG. 3D) and YPBS-L group (FIG. 3E) is considerably improved compared to the model group, as is the number of spermatogenic cells at all levels and the shape of the seminal tubule cavity.

2.3.3 Analysis of Semen Parameters

One side of epididymis in each group is put into a 12-well plate, diluted with 500 μL of normal saline, fully cut into pieces by a tissue scissor, incubated in a 37° C. incubator, and filtered by a 200-mesh sieve, and 20 μL of filtrate is collected on a cell counting plate, observed under a microscope, and the number of sperm is counted. Sperm viability, sperm motility and malformation rate are counted respectively by Yin Hong aniline black and Diff-Quick staining. Data is analyzed using GraphPad Prism 8.4 statistical software. Counting data of experimental results is expressed as rate/percentage (%), and measurement data is expressed as $\bar{x}\pm s$. The one-way ANOVA is used to compare the groups, and the difference is statistically significant with P<0.05. The results are shown in Table 3.

TABLE 3 comparison of semen parameters and testosterone levels in the mice of each group

| Group | n | Sperm count (10⁶/L) | Sperm motility (%) | Sperm viability (%) | Sperm malformation rate (%) | Testis coefficient (%) | Epididymis coefficient (%) | Seminal vesicle gland coefficient (%) |
|---|---|---|---|---|---|---|---|---|
| Con | 6 | 86.17 ± 10.02 | 52.26 ± 3.30 | 63.44 ± 8.59 | 39.44 ± 2.61 | 0.71 ± 0.05 | 0.32 ± 0.03 | 1.26 ± 0.09 |
| Model | 6 | 58.60 ± 6.16* | 21.01 ± 1.59* | 27.49 ± 4.28* | 82.01 ± 8.68* | 0.49 ± 0.07* | 0.20 ± 0.026* | 0.85 ± 0.14* |
| Met | 6 | 85.02 ± 10.55$^\Delta$ | 34.55 ± 0.37$^\Delta$ | 43.84 ± 3.59$^\Delta$ | 68.18 ± 4.12$^\Delta$ | 0.65 ± 0.04$^\Delta$ | 0.33 ± 0.03$^\Delta$ | 1.21 ± 0.06$^\Delta$ |
| YPBS-H | 6 | 83.53 ± 4.44$^\Delta$ | 40.29 ± 3.20$^{\Delta\blacktriangle}$ | 48.71 ± 1.96$^\Delta$ | 66.22 ± 2.14$^\Delta$ | 0.64 ± 0.03$^\Delta$ | 0.33 ± 0.02$^\Delta$ | 1.13 ± 0.14$^\Delta$ |
| YPBS-L | 6 | 80.43 ± 2.66$^\Delta$ | 32.95 ± 1.81$^\Delta$ | 38.87 ± 5.72 | 68.06 ± 6.12$^\Delta$ | 0.64 ± 0.09$^\Delta$ | 0.31 ± 0.04$^\Delta$ | 1.09 ± 0.06$^\Delta$ |

As shown in Table 3, the testis coefficient, epididymis coefficient, and seminal vesicle gland coefficient of the mice in the model group decrease significantly ($p<0.01$) compared to the control group, and the testis coefficient, epididymis coefficient, and seminal vesicle gland coefficient of the mice in the YPBS-H and YPBS-L groups increase significantly ($p<0.05$) compared to the model group. In terms of sperm parameters, the sperm count, sperm viability, and sperm motility of the mice in the model group decrease significantly compared to the control group, while the sperm malformation rate increases significantly ($p<0.01$), and when compared to the model group, the YPBS-H group significantly reverses this situation ($p<0.05$), however, the sperm motility of the mice in the YPBS-H group is greater than that of the mice in the metformin group ($p<0.05$). The traditional Chinese medicine compound provided by the disclosure can improve the sperm count of obese type 2 diabetic mice, the sperm count and vitality obviously increase, the malformation rate decreases, the male reproductive function damage of diabetic mice is effectively improved, and the semen parameters are improved, especially in the YPBS-H group.

2.4 Oxidative Stress Parameters and Testosterone Testing

The levels of T-SOD, MDA and GSH-px in serum are measured by colorimetry, and the level of testosterone (T) in serum is measured by enzyme linked immunosorbent assay (ELISA), all according to the manufacturer's instructions. Data is analyzed using GraphPad Prism 8.4 statistical software. Counting data of experimental results is expressed as rate/percentage (%), and measurement data is expressed as $\bar{x}\pm s$. The one-way ANOVA is used to compare the groups, and the difference is statistically significant with $P<0.05$. The results are shown in Table 4.

species (ROS). Long-term hyperglycemia will lead to excessive ROS production, lead to oxidative stress, promote germ cell death and interfere with spermatogenesis. The oxidative stress is one of the most important pathogenesis of sperm dysfunction. Testosterone is very important for spermatogenesis, and studies have shown that diabetes can reduce the level of testosterone in serum.

As can be seen from Table 4, compared with the control group, the levels of T-SOD and GSH-Px in the serum of the mice in the model group decrease significantly, and the level of MDA increases significantly ($P<0.01$). Compared with the model group, the levels of T-SOD and GSH-Px in the serum of the mice in the YPBS-H group increase significantly, and the level of MDA decreases significantly ($P<0.05$). The traditional Chinese medicine compound provided by the disclosure can improve the contents of T-SOD and GSH-Px in serum of obese type 2 diabetic mice with testicular dysfunction, reduce the content of MDA, and improve the oxidative stress level of obese type 2 diabetic mice with testicular dysfunction.

The testosterone level of the mice in the model group is lower than that of the mice in the control group, and the testosterone level of the mice in the YPBS-H group is significantly higher than that of the mice in the model group ($P<0.01$) and better than that of the mice in the metformin group ($P<0.05$). After being treated by the traditional Chinese medicine compound, the testosterone level of obese type 2 diabetic mice can be increased.

2.3.5 Western Blot is Used to Detect the Expressions of PI3K, p-AKT and Bcl-2 in Testis.

Protein samples are taken and added into concentrated gel of an electrophoresis tank for running the gel, transferring the protein from the gel to the membrane, bovine albumin

TABLE 4 contents of T-SOD, MDA, GSH-Px and T in the serum of the mice in each group

| Group | T-SOD (U/mgprot) | MDA (umol/L) | GSH-Px (umol/L) | Testosterone T(ng/mL) |
|---|---|---|---|---|
| Con | 186.0 ± 19.8 | 5.0 ± 1.5 | 4196.0 ± 265.8 | 5.79 ± 1.11 |
| Model | 124.0 ± 11.5* | 9.5 ± 1.4* | 1309.0 ± 121.3* | 1.39 ± 0.37* |
| Met | 168.4 ± 34.7$^\Delta$ | 5.6 ± 1.5$^\Delta$ | 2206.0 ± 535.6$^\Delta$ | 5.06 ± 1.42 |
| YPBS-H | 179.0 ± 26.6$^\Delta$ | 6.8 ± 1.2$^\Delta$ | 2706.0 ± 583.6$^\Delta$ | 10.33 ± 0.86$^{\Delta\blacktriangle}$ |
| YPBS-L | 170.0 ± 11.6$^\Delta$ | 6.4 ± 2.0$^\Delta$ | 2287.0 ± 154.2$^\Delta$ | 2.08 ± 1.27 |

PI3K/AKT plays a key role in the regulation of insulin signal, apoptosis, proliferation, differentiation and intermediary metabolism. PI3K/AKT, as a classical insulin signaling pathway, is also an important target for the treatment of T2DM. In the diabetes mellitus, the damage of PI3K/AKT pathway is considered to be the main cause of insulin resistance caused by the rising level of reactive oxygen (BSA) blocking and membrane washing, then primary antibodies (including PI3K (rabbit antibody), AKT (rabbit antibody), p-AKT (rabbit antibody), β-actin (rabbit antibody), Bcl-2 (rabbit antibody) and β-actin (mouse antibody) diluted at the concentration 1:1000) are added for incubation and stay overnight in the refrigerator at 4° C.; the next day, the membrane is washed, after the secondary antibodies (including: a mouse secondary antibody (1:5000) and a rabbit secondary antibody (1:2000)) are added for incubation and blocked, the membrane is washed, followed by development, and then gray values are analyzed. Data is analyzed using GraphPad Prism 8.4 statistical software. Counting data of experimental results is expressed as rate/percentage (%), and measurement data is expressed as $\bar{x}\pm s$. The one-way ANOVA is used to compare the groups, and the difference is statistically significant with $P<0.05$. The results are shown in Table 5 and FIG. 4.

TABLE 5 expressions of PI3K, p-AKT and Bcl-2 proteins in testis of the mice in each group ($\bar{x} \pm s$)

| Group | PI3K/β-actin | p-AKT/AKT | Bcl-2/β-actin |
|---|---|---|---|
| Con | 0.880 ± 0.061 | 0.924 ± 0.143 | 0.926 ± 0.037 |
| Model | 0.598 ± 0.107* | 0.581 ± 0.177* | 0.687 ± 0.019* |
| Met | 0.945 ± 0.056$^\Delta$ | 0.635 ± 0.141 | 1.020 ± 0.076$^\Delta$ |
| YPBS-H | 0.899 ± 0.088$^\Delta$ | 0.924 ± 0.237$^\Delta$ | 0.862 ± 0.108$^\Delta$ |
| YPBS-L | 0.827 ± 0.046 | 0.836 ± 0.196$^\Delta$ | 0.623 ± 0.064 |

PI3K/AKT is related to oligoasthenotspermia, and PI3K is considered as a key regulator of sperm motility, overactivation and acrosome reaction. PI3K/AKT is involved in many stages of male reproduction, including regulating the axis of hypothalamus-pituitary-gonad (HPG) during spermatogenesis, and regulating the proliferation and differentiation of spermatogonia and somatic cells. When the activity of PI3K is inhibited, sperm will undergo a cascade of apoptosis, one of which is the rapid loss of motor ability. AKT not only plays a key role in controlling cell survival and apoptosis, but also participates in the regulation of spermatogenesis and sperm motility. Bcl-2, as the downstream gene of AKT, regulates the cell cycle, promotes cell proliferation, inhibits apoptosis, and maintains sperm motility.

Figure 4:
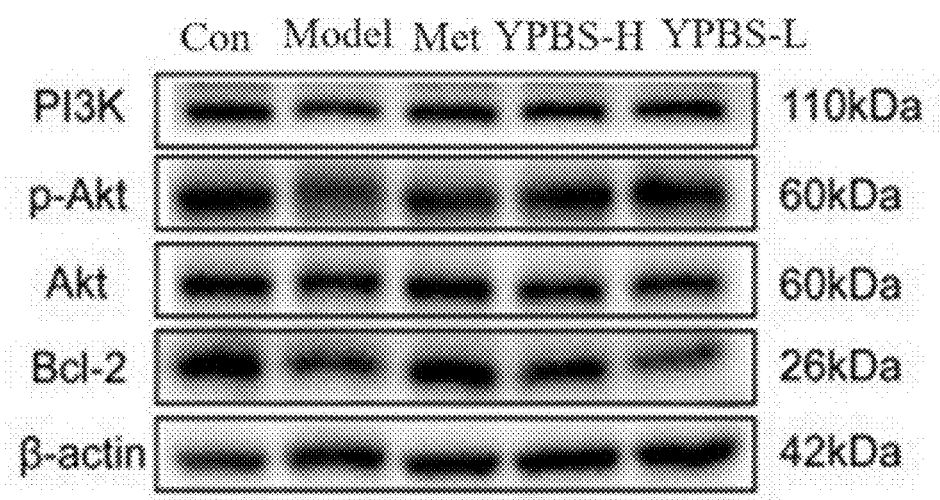
FIG. 4 illustrates a schematic diagram showing effects of different treatments on expressions of PI3K, p-AKT and Bcl-2 proteins in testes of mice with testicular dysfunction caused by obese type 2 diabetes mellitus.

According to Table 5 and FIG. 4, compared with the control group, the expressions of PI3K, p-AKT and Bcl-2 in the model group are significantly down-regulated ($P<0.05$), and the expressions of PI3K, p-AKT and Bcl-2 are significantly up-regulated ($P<0.05$) after the treatment with the traditional Chinese medicine compound. The traditional Chinese medicine compound provided by the disclosure can improve the gene expression of PI3K, p-AKT and Bcl-2 in obese type 2 diabetic mice with testicular dysfunction, and inhibit the apoptosis of spermatogenic cells.

2.3.6 Cage Experiment

Female mice of childbearing age are caged with male mice of each group in the ratio of 2:1 for one week, and their fertility is tested by the birth situation. The experiment shows that, compared with the control group, the fertility of obese type 2 diabetic mice is greatly damaged, and no offspring are produced. However, after treatment with the metformin and the traditional Chinese medicine compound provided by the disclosure, the fertility of the mice is improved, reaching the normal fertility level.

Through the cage experiment, it is confirmed that the Chinese medicinal compound provided by the disclosure can improve the fertility of mice with spermatogenic dysfunction caused by obesity type 2 diabetes.

TABLE 6 experimental results of fertility of mice in each group

| Group | Male mice | Female mice | Vaginal suppository (%) | Pregnancy rate (%) | Average number of offspring |
|---|---|---|---|---|---|
| Con | 4 | 8 | 50 | 37.5 | 7.7 |
| Model | 4 | 8 | 0 | 0 | 0 |
| Met | 4 | 8 | 50 | 50 | 5.3 |
| YPBS-H | 4 | 8 | 50 | 50 | 8.5 |
| YPBS-L | 4 | 8 | 37.5 | 37.5 | 8 |

2.3.7 In Vitro Fertilization

The sperm of the mice in each group is taken for fertilization in vitro. Compared with the mice in the control group, it is found that in the model group, the binding ability between sperm and egg cells is poor, and even after the fertilization, fertilized eggs could not develop normally. However, after treatment with the metformin and the traditional Chinese medicine compound provided by the disclosure, the binding rate of sperm and egg cells increases, and the fertilized egg cells divide normally.

TABLE 7 experimental results of in vitro fertilization of mice in each group

| Group | Egg cell number | Sperm and egg binding number | Number of division of fertilized eggs within 24 hours |
|---|---|---|---|
| Con | 10 | 10 | 10 |
| Model | 10 | 2 | 0 |
| Met | 10 | 7 | 7 |
| YPBS-H | 10 | 9 | 9 |
| YPBS-L | 10 | 7 | 6 |

Through in vitro fertilization, it is further verified that the traditional Chinese medicine compound provided by the disclosure can further improve the spermatogenic dysfunction caused by obesity type 2 diabetes.

According to the above contents, it can be seen that the traditional Chinese medicine compound provided by the disclosure can improve the morphology of mouse testis and the function of semen parameters, and improve testicular dysfunction by promoting glucose uptake, increasing the functional sensitivity of islets and promoting the expressions of PI3K, p-AKT and Bcl-2 genes; and the traditional Chinese medicine compound provided by the disclosure can improve the fertility of mice with spermatogenic dysfunction caused by obesity type 2 diabetes, so that they can reach the normal fertility level. Moreover, the traditional Chinese medicine compound provided by the disclosure can improve the binding rate of mouse sperm and egg cells, make fertilized eggs divide normally, and further improve the spermatogenic dysfunction caused by obesity type 2 diabetes.

Although the above embodiments provide a detailed description of the disclosure, they are only a part of the embodiments, not all of them. Those skilled in the art can also obtain other embodiments based on the embodiments without creativity, all of which fall within the scope of protection of the disclosure.

What is claimed is:

1. A method of improving testicular dysfunction, comprising: applying a traditional Chinese medicine compound to a subject in need thereof, wherein the traditional Chinese medicine compound is made from the following raw materials in parts by weight:

10-40 parts of *Codonopsis pilosula*, 15-100 parts of *Astragalus membranaceus*, 10-40 parts of *Dioscorea opposita*, 6-25 parts of *Angelica sinensis*, 6-40 parts of *Atractylodes macrocephala*, 10-30 parts of *Poria cocos*, 10-30 parts of *Cynanchum otophyllum*, 6-15 parts of *Psoralea corylifolia*, 6-20 parts of *Ligusticum chuanxiong*, 6-20 parts of *Nelumbo nucifera*, 6-20 parts of *Euryale ferox*, 3-10 parts of *Amomum villosum*, 3-10 parts of *Alpinia katsumadai*, 6-20 parts of *Foeniculum vulgare*, 3-15 parts of *Cinnamomum cassia*, 6-10 parts of *Evodia rutaecarpa*, 6-15 parts of *Piper nigrum*, 6-15 parts of *Zingiber officinale*, 6-15 parts of *Aconitum carmichaelii*, and 6-10 parts of *Glycyrrhiza uralensis*.

2. The method as claimed in claim 1, wherein the testicular dysfunction comprises a testicular dysfunction caused by diabetes mellitus.

3. The method as claimed in claim 2, wherein the testicular dysfunction caused by the diabetes comprises: a testicular dysfunction caused by obese type 2 diabetes mellitus.

4. The method as claimed in claim 1, before the step of applying the traditional Chinese medicine compound to the subject in need thereof, further comprising:

mixing the raw materials to obtain a mixture; mixing the mixture with water according to a weight-volume ratio of 136-500 grams (g):400-1000 milliliters (mL), soaking the mixture in the water for 30 minutes (min), decocting the mixture soaked in the water on a high heat until the mixture soaked in the water boils to obtain boiled materials, then decocting the boiled materials on a gentle heat for 40-60 min to obtain decocted materials, and filtering the decocted materials to obtain the traditional Chinese medicine compound.

5. A method of improving at least one of testicular morphology and semen parameters, comprising: applying a traditional Chinese medicine compound to a subject in need thereof, wherein the traditional Chinese medicine compound is made from the following raw materials in parts by weight:

10-40 parts of *Codonopsis pilosula*, 15-100 parts of *Astragalus membranaceus*, 10-40 parts of *Dioscorea opposita*, 6-25 parts of *Angelica sinensis*, 6-40 parts of *Atractylodes macrocephala*, 10-30 parts of *Poria cocos*, 10-30 parts of *Cynanchum otophyllum*, 6-15 parts of *Psoralea corylifolia*, 6-20 parts of *Ligusticum chuanxiong*, 6-20 parts of *Nelumbo nucifera*, 6-20 parts of *Euryale ferox*, 3-10 parts of *Amomum villosum*, 3-10 parts of *Alpinia katsumadai*, 6-20 parts of *Foeniculum vulgare*, 3-15 parts of *Cinnamomum cassia*, 6-10 parts of *Evodia ruticarpa*, 6-15 parts of *Piper nigrum*, 6-15 parts of *Zingiber officinale*, 6-15 parts of *Aconitum carmichaelii*, and 6-10 parts of *Glycyrrhiza uralensis*.

6. The method as claimed in claim 5, before the step of applying a traditional Chinese medicine compound to a subject in need thereof, further comprising:

mixing the raw materials to obtain a mixture; mixing the mixture with water according to a weight-volume ratio of 136-500 grams (g):400-1000 milliliters (mL), soaking the mixture in the water for 30 minutes (min), decocting the mixture soaked in the water on a high heat until the mixture soaked in the water boils to obtain boiled materials, then decocting the boiled materials on a gentle heat for 40-60 min to obtain decocted materials, and filtering the decocted materials to obtain the traditional Chinese medicine compound.

\* \* \* \* \*